(12) United States Patent
Castleberry et al.

(10) Patent No.: US 11,730,884 B2
(45) Date of Patent: Aug. 22, 2023

(54) IMPLANTABLE EXTERNALLY DRIVEN FLUID DELIVERY SYSTEM

(71) Applicant: ForCast Orthopedics, Inc., Longmont, CO (US)

(72) Inventors: Jeffrey Paul Castleberry, Longmont, CO (US); David G. Matsuura, Solana Beach, CA (US); Jacob A. Moebius, Encinitas, CA (US); Philip J. Simpson, Escondido, CA (US); Keir Hart, Lafayette, CO (US); Leo Whiteside, St. Louis, MO (US); Jared Ruben Hillel Foran, Denver, CO (US)

(73) Assignee: ForCast Orthopedics Inc., Longmont, CO (US)

( * ) Notice: Subject to any disclaimer, the term of this patent is extended or adjusted under 35 U.S.C. 154(b) by 443 days.

(21) Appl. No.: 17/011,178

(22) Filed: Sep. 3, 2020

(65) Prior Publication Data

US 2021/0069409 A1    Mar. 11, 2021

Related U.S. Application Data

(60) Provisional application No. 62/896,152, filed on Sep. 5, 2019.

(51) Int. Cl.
| | |
|---|---|
| *A61M 5/142* | (2006.01) |
| *A61M 5/168* | (2006.01) |
| *A61M 5/145* | (2006.01) |

(52) U.S. Cl.
CPC .... *A61M 5/14276* (2013.01); *A61M 5/14212* (2013.01); *A61M 5/14586* (2013.01);
(Continued)

(58) Field of Classification Search
CPC .......... A61M 5/14593; A61M 5/14212; A61M 5/14276; A61M 5/14208; A61M 5/14586;
(Continued)

(56) References Cited

U.S. PATENT DOCUMENTS

| | | |
|---|---|---|
| 9,289,584 B2 | 3/2016 | Chiao et al. |
| 9,381,299 B2 | 7/2016 | Kuo et al. |

(Continued)

OTHER PUBLICATIONS

Notification of Transmittal of the International Search Report and the Written Opinion of the International Searching Authority, or the Declaration dated Nov. 8, 2021, in connection with corresponding International application No. PCT/US 21/46221; 8 pages.

*Primary Examiner* — Jenna Zhang
(74) *Attorney, Agent, or Firm* — Maier & Maier, PLLC (57) ABSTRACT

An implantable externally driven fluid delivery system for localized delivery of medical agents and drugs, such as antibiotics, may be provided herein. The fluid delivery system includes a housing that incorporates a filling septum connected to a flexible internal reservoir. The reservoir is connected to a miniature diaphragm pump with coupled magnetic components. The entire fluid delivery system is implantable into a body cavity or surgically formed location that provides for local medical agent delivery. The reservoir is filled via percutaneous injection through the skin into the septum. Fluid delivery is achieved through proximity of the external controller that generates an oscillating or reversing magnetic field suitable to actuate the pump's diaphragm resulting in controlled fluid flow. Once local drug delivery treatment is complete, the controller can be discarded.

20 Claims, 6 Drawing Sheets

(52) U.S. Cl.
CPC .... *A61M 5/14593* (2013.01); *A61M 5/16804* (2013.01); *A61M 2005/14208* (2013.01); *A61M 2205/3317* (2013.01); *A61M 2205/502* (2013.01); *A61M 2205/8287* (2013.01); *A61M 2210/086* (2013.01)

(58) Field of Classification Search
CPC .. A61M 2205/3317; A61M 2205/8287; A61M 5/14953
See application file for complete search history.

(56) References Cited

U.S. PATENT DOCUMENTS

| | | | |
|---|---|---|---|
| 2004/0147871 A1* | 7/2004 | Burnett | A61M 1/28 604/9 |
| 2007/0112328 A1* | 5/2007 | Steinbach | A61K 9/0024 604/500 |
| 2009/0209945 A1* | 8/2009 | Lobl | A61M 5/14276 709/201 |
| 2012/0226265 A1* | 9/2012 | Chiao | A61M 31/002 604/131 |
| 2013/0086982 A1* | 4/2013 | Miesel | G01F 17/00 73/149 |
| 2014/0142556 A1* | 5/2014 | Kuo | A61M 5/168 604/408 |
| 2015/0025509 A1 | 1/2015 | Jolly et al. | |
| 2020/0289995 A1 | 9/2020 | Di Carlo et al. | |

\* cited by examiner

IMPLANTABLE EXTERNALLY DRIVEN FLUID DELIVERY SYSTEM

CROSS-REFERENCE TO RELATED APPLICATIONS

The present patent application claims benefit and priority to U.S. Provisional Patent Application No. 62/896,152 filed on Sep. 5, 2019, which is hereby incorporated by reference into the present disclosure.

BACKGROUND

Treatment of many medical conditions is challenged by the need to regularly and safely administer medical agents, e.g. antibiotics, chemotherapy or other oncologic therapeutic agents, biotechnology agents, etc. locally at or near the site of the condition to treat over time. One such method of drug delivery is repeated serial local administration (e.g. subcutaneous, intramuscular, intracapsular, intravenous injections) by a clinician. Another method is drug delivery via a reservoir/pump system that allows automatization of the delivery from a reservoir and less frequent administration by a clinician. Furthermore, many diseases are better treated if the therapeutic agent is administered in a manner that is able to achieve a specific concentration or level in the region of interest. Finally, controlled local administration may mitigate the risks inherent to systemic (i.e. intravenous) administration.

In many cases, a medical agent may put the patient at risk of harmful side effects through systemic exposure that are not of concern when administered locally. For example, the use of antibiotics to treat a total joint infection, such as PJI (periprosthetic joint infection). Under the current standard of care, a PJI patient is typically administered an antibiotic, such as vancomycin, through a PICC (Peripheral Intravenous Central Catheter) line with the intention of increasing the blood serum concentration of the antibiotic to near, but below the safe, AKI (Acute Kidney Injury) limit.

Yet, the joint infection resides within a protective anatomical structure, the joint capsule's synovial barrier, wherein the lack of local vasculature inhibits the transfer of antibiotic concentration from the blood stream into the synovial fluid where it is needed to directly treat the infection. The result is that to achieve even modest intra-capsular concentrations, the patient may be exposed to high systemic concentrations which can contribute to other side effects. Meanwhile only a low concentration, many times at sub-therapeutic levels, can be achieved at the site of infection. Exposure at subtherapeutic levels is considered a primary cause for the development of antibiotic resistance. Without the means of directly applying the antibiotic to the bacterial infection within the joint capsule, the indirect, systemic treatment is suboptimal and may be counterproductive. Alternatively, external infusion pumps can be employed using sterile tubing as the drug conduit between the pump and the patient. Typically, the tubing is continuously connected to some form of implanted port or catheter to direct the medical agent to a targeted location. The surface skin exposure or access point can present a significant burden for hygiene to minimize the potential for infection at the site, especially for therapies that may require weeks or months of continual treatment. Alternatively, implantable drug delivery devices attempt to achieve better medical agent therapy by delivering specific amounts of an agent to a specific targeted body cavity or location on a prescribed frequency over an extended duration without surface skin or access site continuous exposure. These implanted delivery devices may also protect the medical agent in an onboard reservoir whereas the agent may not be stable under longer exposure in vivo, e.g. in contact with tissues or vasculature, and as such would instead require frequent, local dosing intervals that are a significant burden to the clinician and patient. Implantable drug delivery devices can include polymeric implants, implantable osmotic pump systems, and electromechanical infusion pumps.

Polymeric implants, used extensively in controlled drug delivery systems, include non-degradable polymeric reservoirs and matrices, and biodegradable polymeric devices. In both cases the drug is released by first absorption (or solubility) into the polymer and then diffusion through the walls of the polymeric device into the patient. The release kinetics of drugs from such systems depends on both the solubility and diffusion coefficient of the drug in the polymer, the drug load, and, in the case of the biodegradable systems, the degradation rate of the polymer in vivo which may vary depending upon the target location. Examples of polymeric implants include micro-sized, bead or sphere reservoirs of medication surrounded by a polymeric membrane and homogeneous dispersions of drug particles throughout a solid matrix of non-degradable polymers.

In orthopedics, this delivery approach is used in temporary antibiotic impregnated bone cement spacers and beads typically fabricated from polymethylmethacrylate (PMMA). In both cases of spacers and beads, these devices are temporary and must be removed after the antibiotic is exhausted and therapy is finished. Biodegradable polymeric devices are formed by physically entrapping drug molecules into matrices, sponges or microspheres. These polymers dissolve when implanted or injected and release drugs. In each of these examples, the amount of drug available to deliver is limited by the initial load, or charge. As the drug is released, the charge is exhausted and the delivery rate of the drug decays with time. If the duration of high delivery rate is too short for the planned drug therapy, the first device may need to be removed and a second device implanted or injected, thus again burdening the clinician and the patient with repeated procedures. Implanted drug delivery devices that use an active delivery pumping mechanism to deliver a medical agent can overcome this limitation.

Another method for controlled prolonged delivery of a drug is the use of an implantable osmotic pump, e.g. Alzet Osmotic Pumps, CA. An osmotic pump is generally in a capsule form having permeable walls that allow the passing of water into the interior of the capsule containing a drug agent. The absorption of water by the water-uptaking drug composition within the capsule reservoir creates an osmotic pressure within the capsule to push the drug out of the capsule to the treatment site. The length of prolonged delivery is limited by the size of the osmotic pump reservoir and may require surgical removal and replacement if treatment is not yet completed when the reservoir is empty.

Implantable devices for drug diffusion delivery usually include a permeable or micro-porous membrane for controlled diffusion of a drug into the body from a suitable reservoir that is placed at or in the target treatment site. Such devices are limited in application primarily since the rate at which the drug is delivered to the body is completely dependent upon the rate of diffusion through the permeable membrane, which is changing over time as the reservoir concentration diminishes and the surrounding fluid concentration increases. Likewise, the rate of drug diffusion may change due to fouling of the permeable membrane over time. With these devices the rate of drug delivery to the body may be also affected by differing conditions within the body, e.g. hydration, pH, etc. In addition, such systems make no provision for the adjustment of the rate or time interval for drug delivery, nor can the delivery rate be easily varied. As previously noted, the length of prolonged delivery is limited by the size of the diffusion reservoir and may require surgical removal and replacement if treatment is not yet completed when the reservoir is empty.

Although polymeric implants, osmotic pumps and diffusion reservoirs may provide a steady, though declining, rate of drug release for a specific period, some medical agents are more effective when administered in intervals or via bolus dosing over time. Implantable electromechanical infusion pumps can be programmed to deliver drugs at consistent and specific dosages, delivery rates and intervals. Further, these pumps may have a feedback device that controls drug delivery according to need. With the current development of electronics and miniaturization of pumps and sensors, various vital signs can be monitored leading to feedback systems such as for monitoring blood glucose levels and delivering insulin when needed, as an example.

These implantable, electromechanical infusion pumps typically incorporate the use of an internal power source, e.g. a battery, electronic controls and a form of motor or displacement driver to motivate the medical agent for infusion, e.g. Synchromed Programmable Pumps, Medtronic, TN. They may be recharged through an external inductive coupling circuit. They may have an external controller/programmer accessory that allows for delivery adjustment over time with a form of wireless communication to the pump, e.g. Bluetooth, etc. They may also have capabilities to allow the internal drug reservoir to be periodically refilled through a needle injection through the skin and into a septum incorporated into the reservoir housing. Given their complex construction and incorporation of enclosed toxic elements (electronics and batteries), these pumps are placed surgically and typically removed surgically when treatment is concluded, or the pump life has been exhausted and must be replaced. Given their complexity, these pumps are expensive and therefore not economically suitable for certain uses. Further, their complexity also contributes to greater potential for device failure, resulting in a potential for patient injury, and/or the need for more frequent surgical removal and replacement.

SUMMARY

According to an exemplary embodiment, an implantable drug delivery device may comprise a miniature pump and reservoir. The pump may comprise a miniature diaphragm incorporating a magnetic element on the primary pump diaphragm. The miniature pump design may use passive, normally closed valves to assure the proper directional flow of the medical agent. The valves may open and close based upon minimum differential pressure. The inlet to the pump may be placed within, or connected to, a refillable reservoir that may hold a certain volume of a desired medical agent. The outlet to the pump may be placed to deliver the medical agent directly into the pump's implanted location within a body cavity or other anatomical location, or infuse into a connected catheter to translate the medical agent delivery to an adjacent targeted location. The diaphragm may contain an integrated magnetic component to facilitate movement of the diaphragm through an independent and separate electromagnetic field exerted on the magnetic component.

The pump may be actuated to deliver the medical agent contained within the reservoir through an oscillating e.g. changing magnetic flux amplitude and/or reversing, magnetic field produced by an external controller worn or held against the patient's skin and acting on the magnetic component of the primary pump diaphragm without direct contact. The magnetic field transverses and penetrates the skin and tissue residing between the implanted pump and the external controller. The external controller may be placed in the proper position adjacent/over the implanted pump location to properly align the magnetic field with the diaphragm magnet. Separate and independent positioning means, e.g. magnets, in the implanted infusion pump housing may trigger associated sensors within the external controller to verify the placement on the patient's skin at which the external controller provides visual indication of proper position to the user attempting to properly position the controller, prior to the controller attempting pump function. Additionally, the external controller may monitor magnetic flux and provide an indication of whether a magnetic component of the pump, such as a magnet or valve magnet is moving.

The magnetic field generated by the controller may be sufficiently strong and may be specifically directed to transcend the thickness of soft tissue and skin between the controller and the magnetic pump. A delivery catheter may allow the implanted pump to be placed near the skin while treating an anatomical location too deep or otherwise obscured for the magnetic field to effectively reach and operate the pump.

The reservoir may provide for one or more subdermal septa that can be properly located for subcutaneous needle injection for refilling the reservoir. These septa may be located via palpation, ultrasound imaging or fluoroscopic imaging to assure proper needle advancement.

The external controller may be programmable to allow for adjusting the dosage amount, the frequency of the dosage delivery, and the schedule of the dosage delivery. T h e do sage may be a bolus of medication. The controller may be configured for wear by the patient, e.g. incorporated into a limb or body wrap, or a simple hand-held device placed over the implanted pump site used only during the delivery schedule and held in the proper position. The external controller may monitor for key parameters such as proper position, diaphragm magnet movement, such as a pump stroke, drug delivery flow, reservoir volume and may record these events to provide use history for clinician monitoring including assessment of patient compliance.

Given the implantable magnetically driven infusion pump and reservoir's construction, which may not include batteries, a motor, bellows filled with a compressible fluid, or electronic components, the fluid delivery system may be biocompatible and suitable for being retained with the patient's body as a lifetime implant without toxicological risk due to material or mechanical degradation over time. At the conclusion of the fluid delivery treatment, the external controller may be discarded, leaving nothing on or penetrating the surface of the patient's skin.

This externally driven, implanted fluid delivery system may be formed from an external magnetic field generation controller and a magnetically driven implantable infusion pump with reservoir. The external controller and the implanted pump with reservoir comprise a delivery system that may be used to achieve medical agent delivery to a specific dosing schedule to support local delivery and local treatment. Medical agents most likely to be used with this system will have a modest dose error injury risk profile and therefore modest requirements for pump dose accuracy. This may include antibiotics, chemotherapy and other oncology agents, or insulin among other medical agents, e.g. drug or biotechnology solutions.

The implanted pump may be surgically placed subcutaneously but strategically located so as not to interfere with the patient's other anatomical structures or be otherwise obtrusive. The delivery catheter may be connected to the pump and may be surgically placed or tunneled to the target location for directed drug therapy.

In an alternative implementation for externally controlling an implanted infusion delivery system, the external controller may be used to magnetically couple and operate active control valves with or without the magnetically coupled diaphragm pump. These valves may be moved in concert with or separate from a magnetically driven pump. In addition, independent magnetic controlled valves may be used to allow for external control of an implantable infusion delivery system incorporating non-electronically nor magnetically driven internal pump methods. A magnetically controlled valve may provide a controlled drug dose from an implanted elastomeric pump, e.g. an elastomeric balloon or reservoir of drug that may be pressurized through the expanded elastomeric nature of the reservoir.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention," "embodiments," or "invention" do not require that all embodiments of the invention include the discussed feature, advantage, or mode of operation.

According to at least one exemplary embodiment, and referring generally to the Figures, a pump may be shown and described herein. The pump may be formed from a number of components, including but not limited to machined components, molded components, laser cut components, die cut components, thermoformed components. The pump may be constructed of various polymers, elastomers, metals, glass and/or the combination of these materials. The pump may be assembled using adhesive, adhesive layers, various forms of welding (thermally melting components together), or mechanically retained via internal or external holding structures.

According to at least one exemplary embodiment, and referring generally to the figures, a pump may be shown and described herein. The pump may be configured to deliver a fluid, in particular fluid medical agents and drugs, to a patient, whether the pump is implanted in the patient or not. The pump may be configured to advance fluid via a flexing diaphragm, a translating piston in a cylinder, compressing tubing in a sequential manner, or a rotating mechanism, such as vanes. The pump may require a motivating force to generate movement of its mechanism that causes a fluid to advance. A magnetic element may be attached to, or otherwise incorporated within, the mechanism as part of the means to generate the motivating force for movement, when the magnetic element is acted upon by an oscillating magnetic field. The oscillating magnetic field can be generated either through mechanically translating permanent magnets or a generated electromagnetic field. The oscillations of the magnetic field may be achieved by reversing the polarity of the magnetic field over time, or by varying the amplitude of the magnetic field with common polarity over time, or some combination of both. The oscillating magnetic field may be generated by a separate, independent source that is not connected to the pump. The source may be placed adjacent to the implanted pump wherein the oscillating magnetic field transcends the housing of the source and the enclosure of the pump to generate the motivating force for advancing fluid within the pump, whether the pump is implanted or not. The source may be placed external to the patient's body, on or above the skin, but does not pierce the skin or tissue above or around the pump when implanted in the body, while the oscillating magnetic field transcends the skin and tissue between the source the implanted pump to generate the motivating force for advancing fluid within the pump. The oscillating magnetic field can be continuous or intermittent in operation, the latter allowing the source to be temporarily removed from being adjacent to the pump without damage or harm to the pump, source or patient, e.g. the source is incorporated into a patient worn brace or wrap that is temporarily removed from the patient to allow the patient to bathe, etc.

Figure 1:
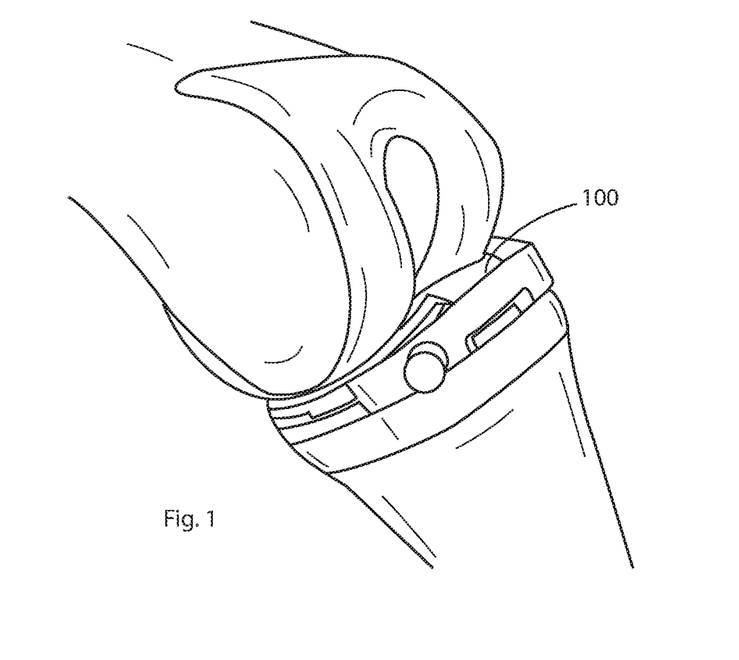
FIG. 1 is a view of an exemplary embodiment of an implantable, externally driven magnetic infusion pump with reservoir incorporated into a total knee replacement, prosthetic knee spacer.

FIG. 1 may depict a view of an exemplary embodiment of a prosthetic knee spacer 100 in accordance with the present invention. The prosthetic knee spacer 100 may be designed for surgical implantation into a knee joint between a femoral condyle and corresponding tibial plateau. In some exemplary embodiments, the prosthetic knee spacer 100 may include an internal magnetically driven implantable infusion pump for drugs or other liquid medical agents. In one exemplary embodiment, the implantable magnetically driven pump, combined with a flexible reservoir, internal within the prosthetic knee spacer, may provide the ability to deliver liquid antibiotics directly into the synovial cavity to mix with synovial fluid and thereby selectively treat a joint infection, such as a periprosthetic joint infection, at the site of the infection.

Figure 2:
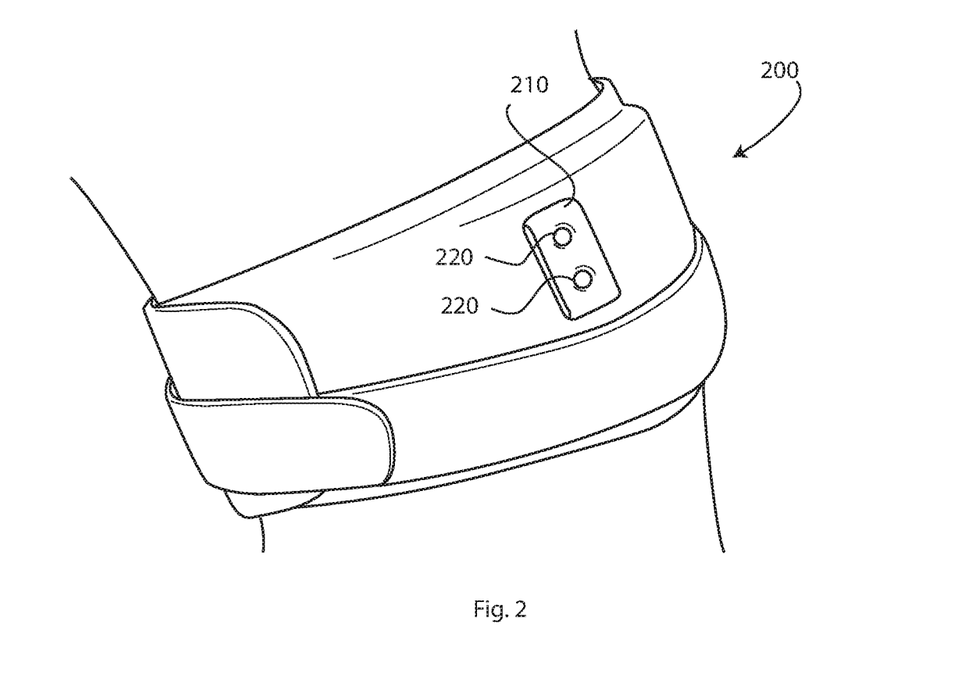
FIG. 2 is a view of an exemplary embodiment of an external controller for magnetic field generation to operate the implanted pump incorporated into a knee wrap or brace.

FIG. 2 may illustrate an exemplary embodiment of a magnetic field controller 200 that is applied to the exterior surface of the knee's skin barrier over the implanted magnetically driven pump. The controller may generate an oscillating magnetic field that may act on the magnetic element in the implanted pump to develop the force on the pump's mechanism that results in pumping movement and fluid delivery. The controller 200 may be constructed within a compliant fabric band that is configured to wrap around a patient's body part or limb, or the controller may be otherwise affixed to the patient's skin through adhesive tape for example, or simply held in place during use, etc. The controller may be removable and only positioned and applied at the Clinician directed times for fluid delivery (dosage). The band may include a power supply, control circuitry, user interface 210 for programming and monitoring fluid delivery and indicators 220, and an oscillating or reversing magnetic field generating system, such as an electromagnetic coil or rotating magnets, that interacts through the patient's skin with components within the implanted fluid delivery system. The control system may facilitate a pumping mechanism, a valving mechanism or both. The controller can be worn continuously or periodically during the treatment period, and may be discontinued after fluid delivery is terminated, such as at conclusion of the medical treatment or the resolution of an infection. As the controller may be removable it can be removed leaving nothing on, or penetrating, the surface of the patient's skin. Meanwhile, the implantable drug delivery system may contain no biologically hazardous materials providing for its ability to be retained as a permanent implant for the life of the patient if that is deemed advantageous for the patient.

In another exemplary embodiment, the magnetic field controller may be placed over an implantable fluid delivery system. The field may operate magnetic valves within the implant to assure positive opening and closing of the fluid path. Multiple magnetic fields may be configured such as to offer a combination of operating a magnetic pumping element and magnetic value elements within the implant. In another embodiment, magnetically operating valves may be most advantageous if an independent, continuous pumping method, such as an implanted elastomeric pump, was employed to advance fluid in the delivery system.

Figure 3:
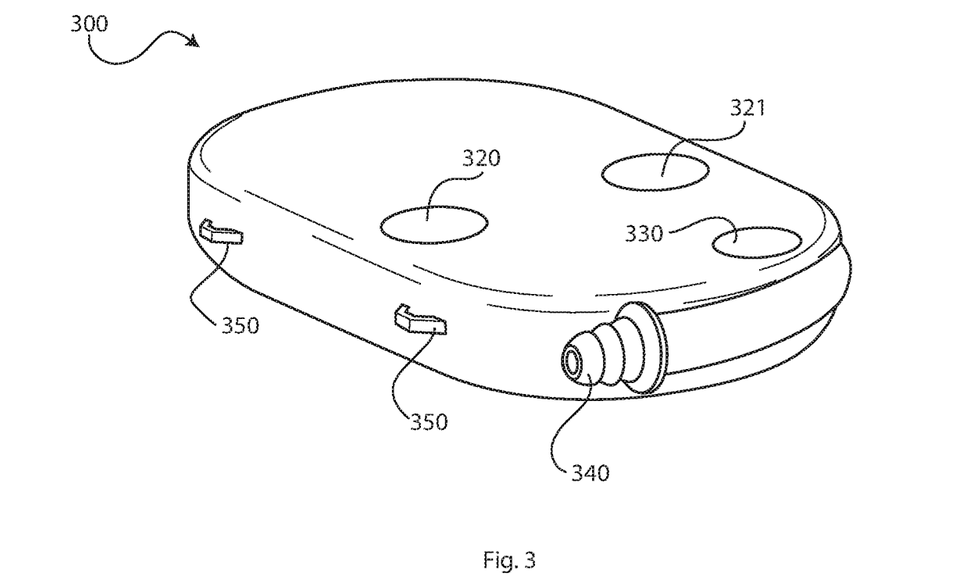
FIG. 3 is a view of an exemplary embodiment of an implantable magnetically driven infusion pump with reservoir in a housing that would be surgically placed in a subdermal pocket.

FIG. 3 may depict an exemplary embodiment of an implantable magnetically driven fluid delivery system 300, an enclosure housing a magnetically driven pump with reservoir, for use in other body cavities or surgically formed spaces, e.g. a subdermal pocket. The implantable fluid delivery system may be accessible from an external source, such as a syringe attached to a needle, via a filling septum 320, 321 or port. In some exemplary embodiments, for example, a soft, elastomeric septum may allow for needle penetration to facilitate subcutaneous injection for refilling the reservoir of the fluid delivery system through the surrounding skin, tissue and septum. The filling septum may connect to the reservoir and prevent leakage of the drug or liquid medical agent. The fluid delivery system may include a connector 340 for a separately connected delivery catheter allowing the housing to be surgically placed near the skin while the catheter translates the drug to a different target location, possibly much deeper in the anatomy, at a location such that the magnetic controller cannot couple sufficiently with an implant for control or be accessible for percutaneous injection for refill. The delivery catheter may also benefit from the use of a flush port 330 to prime and/or confirm fluid flow during surgical placement. The housing of the implanted drug delivery system may include suture anchors 350 placed around the housing to allow the device to be restrained within the surgical site and avoid migration due to body movement over time, assuring alignment of the magnetically driven pump element with the controller generated oscillating magnetic field.

According to an exemplary embodiment, the septum 320, 321 may be protuberant from the surface of the delivery system, which may, for example, facilitate palpation of the septum by an administrating clinician. According to another exemplary embodiment, port may not be protuberant, and may instead be a window; such a window-type port may be flush with or sunk into the hollow outer portion of a spacer, as desired.

Figure 4:
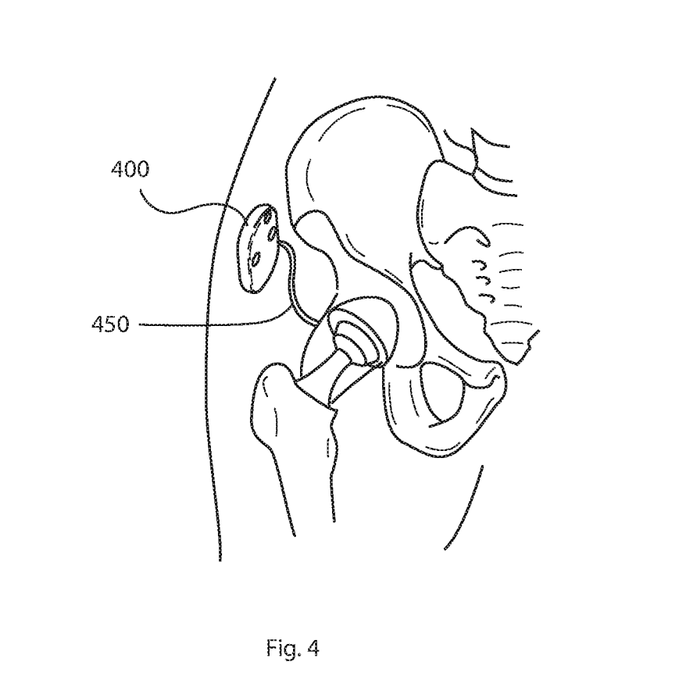
FIG. 4 depicts an exemplary embodiment of a the implantable magnetically drive infusion pump with reservoir placed near the hip connected to a tunneled catheter to delivery antibiotic into the hip synovial capsule.

FIG. 4 may depict a view of an exemplary embodiment of a remotely controlled drug delivery system 400, which may be implanted, in accordance with the present invention. The implanted delivery system 400 may be designed for surgical implantation adjacent to a targeted antibiotic location, e.g. a hip joint. In some exemplary embodiments, the implanted delivery system 400 may include a remotely magnetically driven implantable infusion pump for drugs or other liquid medical agents. In one exemplary embodiment, the implantable magnetically driven pump inside the delivery system 400 and surgically implanted delivery catheter 450 may provide the ability to deliver liquid antibiotics directly into the synovial cavity of the hip to mix with synovial fluid and thereby selectively treat joint infection, such as periprosthetic joint infection, at the site of the infection. As can be envisioned by anyone skilled in the art, any form of liquid medical agent or drug can be delivered in this manner and any orthopedic joint, cavity, potential space, tissue, or organ including any element of the musculoskeltal system, may be treated in this manner.

Figure 5:
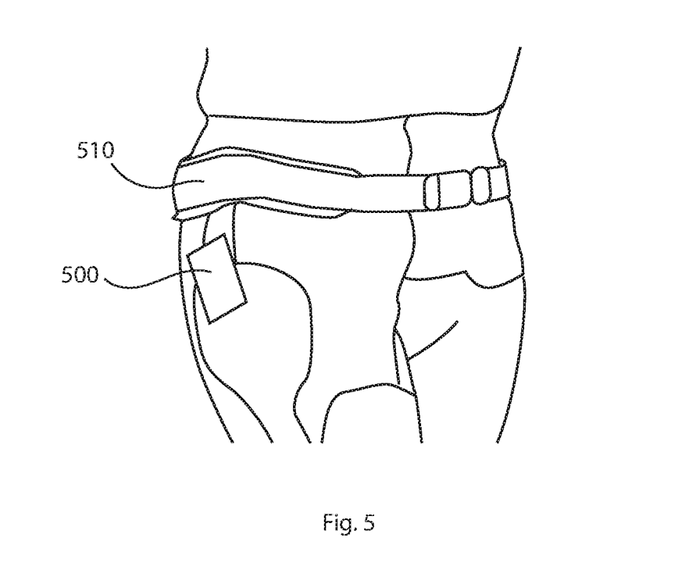
FIG. 5 depicts an embodiment of an external controller for magnetic field generation to operate the implanted pump, shown as integrated into a body wrap hip brace.

In another exemplary embodiment, FIG. 5 may illustrate a magnetic field controller 500 incorporated into another medical device, such as a body wrap hip brace 510. The controller magnetically couples to the implanted delivery system, such as the delivery system 400 illustrated in FIG. 4, to operate the internal pump and thereby deliver the drug to the hip joint, for example, via surgically implanted delivery catheter 450 illustrated in FIG. 4.

Figure 6:
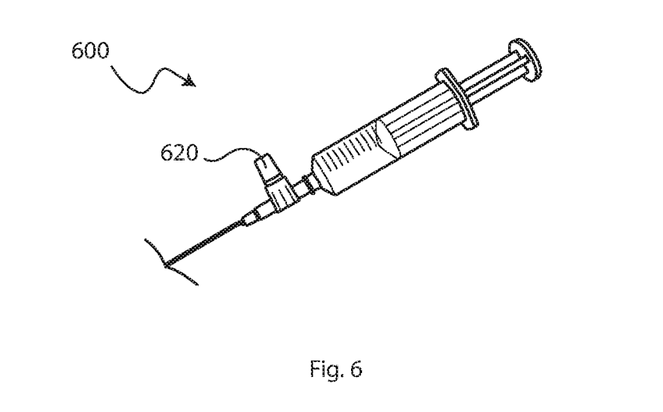
FIG. 6 is a view of a refilling method for the implantable magnetically driven infusion pump with reservoir.

In an exemplary embodiment, FIG. 6 illustrates that the fluid delivery system may be refilled after it is implanted by the application of a percutaneous needle. An administrating clinician may insert the needle through the skin of the patient and into the septum of the spacer, thereby allowing fluid access to an internal reservoir of the delivery system and allowing it to be refilled via the needle, for example with the use of a syringe or a separate pump. Refilling the reservoir may use a pressure monitor. According to an exemplary embodiment, the septum may be made of rubber or another flexible material such that a needle can be inserted through the port numerous times without significantly compromising the ability of the port to seal to retain fluid within the reservoir.

The septum may allow both the addition of and removal of fluid, which may be used in order to change the medical agent. This may be accomplished by drawing the fluid out of the delivery system's reservoir to empty it, e.g. aspirate the contents via a needle access through the septum, and then refill the reservoir with a different drug or medical agent. Additionally, this may allow for fluid levels to be more easily checked to verify pump performance. Alternately, other fluids may be added to the delivery system. For example, in one exemplary embodiment, anticoagulants may be added to prevent clot formation around the delivery system, while in another exemplary embodiment, chemical surfactants may be added to improve fluid delivery, while in another exemplary embodiment, mixtures of drugs may be filled in the reservoir, e.g. a cocktail of antibiotics to concurrently treat multiple bacterial pathogens.

According to an exemplary embodiment, the septum may have a localization marking that allows the port to be localized on X-ray or fluoroscopy. For example, according to an exemplary embodiment, the port may be surrounded by a radio-dense ring that allows the port to be observed in an X-ray or Ultrasound. According to another exemplary embodiment, such as when the port 110 is constructed from a hard material, the port itself may be constructed from a radio-dense material.

FIG. 6 is an exemplary embodiment of a filling (and refilling) method 600 for monitoring injection pressure. At one or more instances within the time period in which the fluid delivery system is in place, it may become depleted past a desirable point. For example, the reservoir of the fluid delivery system may become fully depleted, or sufficiently depleted that the amount of liquid medical agent being dispensed by the fluid delivery system is near a minimum desirable amount or less than a minimum desirable amount. At that point, the fluid delivery system may be refilled percutaneously, for example by the injection of a syringe into the septum. This may allow for the fluid delivery system to be refilled without requiring the full surgical removal and replacement of the empty device with a filled device, which may result in easier maintenance of medical agent levels and greatly reduce cost and morbidity for the patient.

The filling method 600 may operate based upon the requirements of the implantable drug delivery system. The filling method 600 may ascertain whether the reservoir is empty or nearing empty before filling to verify the fluid delivery system is properly working and minimize the potential for overfilling in error which could damage the implanted device. This filling method 600 may include a pressure sensing and indicating means 620 attached to the syringe to minimize the risk of overfilling the reservoir resulting in device damage. The filling method may include the means for aspirating the remaining fluid in the reservoir before or concurrent with filling the reservoir with new liquid medical agent.

Alternately, the fill method 600 may incorporate first aspirating all contents of the internal reservoir to assure it is empty and then filling the reservoir with a known volume of fluid equal to the size of the reservoir without monitoring pressure.

Figure 7:
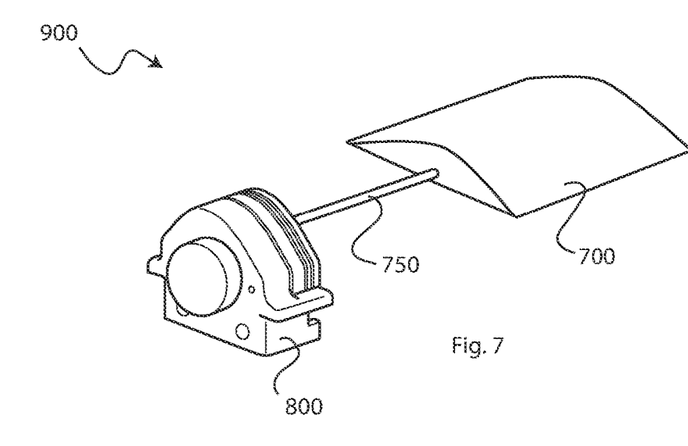
FIG. 7 is a view of an exemplary embodiment of an implantable magnetically driven pump assembly integrated with and attached to a flexible reservoir, these items would be contained within the housing of the fluid delivery system.

FIG. 7 is an exemplary embodiment of an implantable magnetically driven pump assembly 800 integrated with a flexible reservoir 700 as a subassembly 900. FIG. 7 may illustrate the reservoir 700 as an elastomeric bladder in full condition to fit within the internal cavity fluid delivery system housing, whether a knee spacer or an independent enclosure for subdermal placement. The reservoir may be formed of flexible film material panels welded together along a weld line defining a seam, or may be formed by molding as a single component. The reservoir may define a unique shape that, when full, attempts to capture all or the majority of the void (internal cavity) available within the fluid delivery system housing. The implantable electromagnetic pump may reside with or may reside adjacent, connected by a inlet tube 750 but external to the fluid reservoir as a subassembly (as shown in FIG. 7) that resides within the fluid delivery system housing. Thus, depending on which components are intended to be implanted, the implantable electromagnetic pump alone, both the implantable electromagnetic pump and the fluid reservoir, or the implantable electromagnetic pump, the fluid reservoir and the housing contain no biologically hazardous materials so that the one or more components can be retained as a permanent implant(s) for the life of the patient if that is deemed advantageous for the patient.

In some exemplary embodiments, the flexible reservoir 700 may be an elastomeric bladder with components formed by LIM, lost wax, or other molding of elastomeric materials, e.g. silicon, polyurethane, to generate a collapsed shape with minimal residual volume and expand to the available internal cavity when filled.

In other exemplary embodiments, the flexible reservoir 700 may be a blow-molded or thermoformed bladder, with a component molded in its expanded shape to assure minimal, if not zero, pressure generation on the reservoir contents in use. The use of a flexible or compliant reservoir, versus a rigid structure, is to help mitigate the potential risk of fracture in the latter given the environmental stress placed on the implantable fluid delivery system, especially with active patients. Either during medical agent therapy or after therapy is complete and the reservoir is sitting empty/benign within the knee implant for many years, the device may not degrade or fracture (releasing material) within the anatomical site.

In another exemplary embodiment, the flexible reservoir may incorporate a permeable air filter to allow the release of entrapped air as bubbles within the reservoir so as to avoid air bubbles attempting to transition through the magnetically coupled pumping element.

According to an exemplary embodiment, the reservoir 700 may hold one or more fluids, which may be, for example, solutions of antibiotics, steroids, hyaluronic acid, stem cells, anticoagulants, surfactants, chemotherapy agents, analgesics including opioids, antispasmodics, antihypertensive drugs, biotechnology agents including solutions containing nanotube structures, insulin, other medical agents and fluids, or some combination thereof. According to the therapeutic purpose of the fluid, the implantable pump and flexible reservoir in its enclosure may be implanted anywhere in the body (human or animal) in which a surgically formed pocket can be made to accommodate the enclosure below the skin and the delivery catheter tunneled to the appropriate anatomical structure associated with the fluid or drug, e.g. synovial capsule of a joint, specific vasculature, intrathecal canal in the spine, intracranial, intraocular, along the gastrointestinal tract, in the plural cavity, in the lung or along the pulmonary system, in the heart or along the cardiac system, etc.

Figure 8:
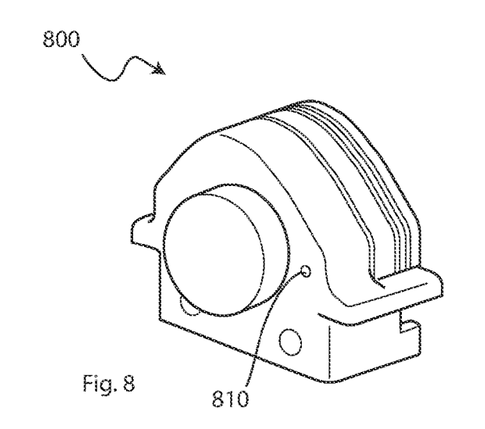
FIG. 8 is a view of an exemplary embodiment of an implantable magnetically driven pump denoting the vent and outlet port.
Figure 10:
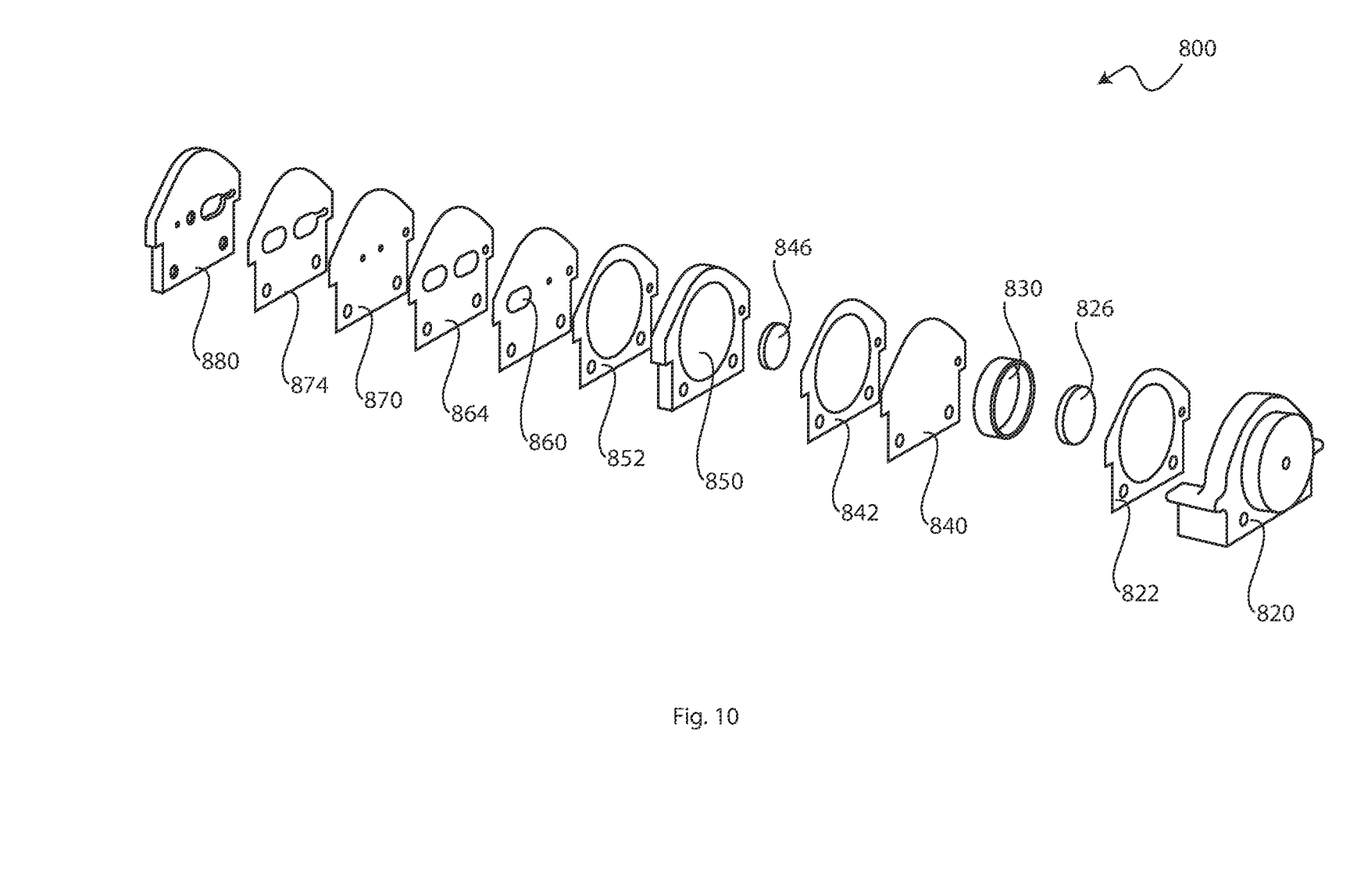
FIG. 10 is an exploded view of an exemplary embodiment of a laminate construction of an implantable magnetically driven pump.

Exemplary FIG. 8 may illustrate an exemplary embodiment of the magnetically driven pump assembly 800. In this exemplary embodiment, the pump assembly may be constructed of unique layers bonded, welded or otherwise joined together to form the pump body. Examples of the unique layers are shown in FIG. 10. Within the body may be the magnetically coupled diaphragm, active valves or passive check valves for directing fluid flow, and fluid flow channels. FIG. 8 may illustrate one location of the fluid delivery outlet port 810 positioned on the pump assembly 800. The outlet port may be positioned anywhere on the periphery of the pump assembly.

Figure 9:
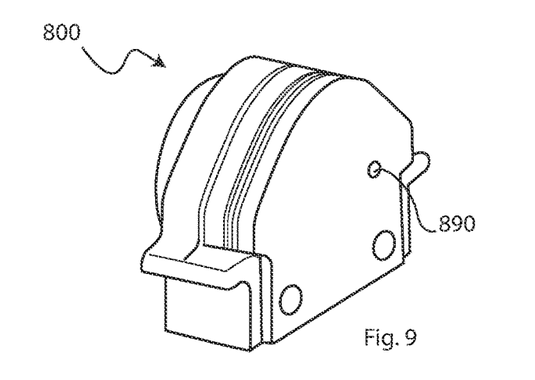
FIG. 9 is a view of an exemplary embodiment of an implantable magnetically driven pump denoting the inlet port.

Exemplary FIG. 9 may illustrate an exemplary embodiment of a magnetically driven pump assembly 800. FIG. 9 may illustrate one location of the fluid delivery inlet port 890 on the pump assembly 800. The inlet port may be positioned anywhere on the periphery of the pump assembly.

Turning now to exemplary FIG. 10, FIG. 10 may illustrate an exemplary embodiment of the componentry used in a magnetically driven pump assembly 800 for fluid infusion by an implantable fluid delivery system, such as the one shown in FIG. 3, which includes an implantable pump and flexible reservoir within an enclosure. In this exemplary embodiment, the pump assembly 800 may be formed from various layers of polymer film, solid polymer, metal and glass that may be laser die cut or machined. The layers may be adhered together with interstitial adhesive or adhesive layers to build the body of the pump, such as pump adhesive layers 852, 842 and 822 shown in FIG. 10. Each end of the pump assembly 800, e.g., the Pump Frame 820 and the Pump Base 880 may be machined or molded components with features to engage the pump with the other elements of the implantable fluid delivery system. The pump diaphragm 840 may be a thin layer of polymer sheet or metal, or a molded polymer component, or formed metal sheet. The magnetic element may comprise multiple magnetic components, such as magnets 826 and 846, may be coupled on either side of the diaphragm 840 along with the magnetic pole 830, or may be a single component that pierces through the diaphragm to be held securely with a leak free joint. In an exemplary embodiment, magnets 826 and 846 may be the same grade, for example N52 neodymium magnets, but differ in size, for example, magnet 846 may be 3/16" in diameter and 1/32" in thickness and magnet 826 may be 3/16" in diameter and 1/16" in thickness. The pump check valve membrane 870 may operate between two check valve adhesive layers 874 and 864 and with the check valve cavity 860 to define the flow path into and from the main pump diaphragm cavity 850. The valve membrane 870 flexes to open and close each of the two valves based upon the differential pressure it experiences across each valve position. This novel construction may allow for very small pump assembly configuration, good performance that can be optimized by dimensional and material changes, and provides for a simple, low cost method of manufacture.

Figure 11:
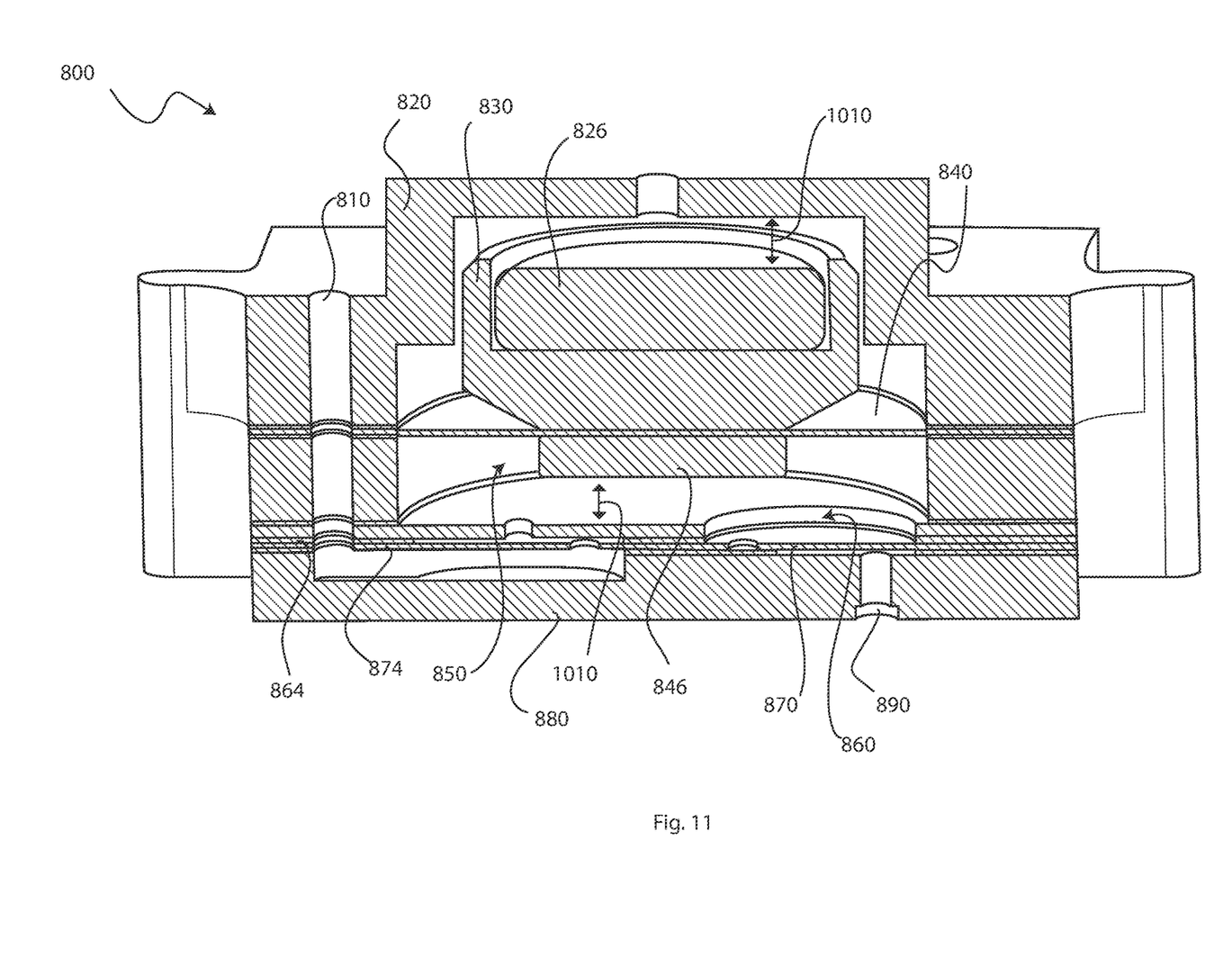
FIG. 11 is a section view of an exemplary embodiment of an implantable magnetically driven pump.

FIG. 11 may illustrate a section view of this exemplary embodiment of the magnetically coupled pump assembly 800 from FIG. 10 in assembled form. This section view highlights that magnet 846 and magnet 826 with magnetic pole 830, are captured against both sides of the diaphragm 840 and the single pump check valve membrane 870 supports the function of both the inlet and exit check valves to assure proper fluid flow direction and performance. Further, the displacement of the magnetically coupled diaphragm 840 is limited by the mechanical enclosure ensuring deflection of the diaphragm is limited to minimize the potential for material failure and reduce the dependency on a specific magnetic flux to achieve full pumping stroke. The stroke length 1010 is then limited on each side of the flexible diaphragm. Therefore, the implantable magnetically coupled pump assembly 800 needs only to be exposed to a minimum magnetic flux to achieve displacement and contact with the mechanical stroke limits. Varying amounts of magnetic flux above this minimum limit will not detrimentally impact the performance of the pumping mechanism.

Figure 12:
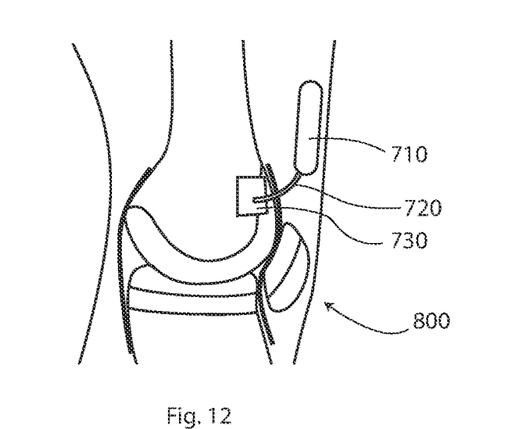
FIG. 12 is a view of an exemplary embodiment of an implantable magnetically driven pump separately placed in the body, specifically within the synovial cavity of the knee joint, and connected to a separate reservoir through a catheter.

In another exemplary embodiment, the implantable magnetically coupled pump 800 is separately placed in the body and connected to a separate reservoir 710 through a catheter 720 as shown in FIG. 12. In this configuration, the enclosed pump is held within the synovial cavity, inside the synovial barrier 740, to be bathed by the synovial fluid with antibiotic concentration which may minimize the potential for the implanted pump and enclosure to become a site of bacterial infection. The catheter penetrates the synovial barrier to connect the pump and enclosure to the reservoir. In this configuration, the reservoir may be larger in size and volume than otherwise could be achieved if the reservoir were integrated with the pump a single enclosure.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments may be made by those skilled in the art without departing from the scope of the invention as defined by the following claims.

What is claimed is:

1. An implantable pump, comprising:
   a plurality of layers bonded to each other so as to form a laminate assembly; and
   a magnetic element configured to cause the implantable pump to function in response to a magnetic field, the magnetic element being separated by a flexible diaphragm into a first magnet portion and a second magnet portion;
   wherein layers of the plurality of layers include apertures defined therein, the apertures defining cavities in the laminate assembly for passage of a fluid therethrough; and
   wherein the implantable pump is configured to respond to a magnetic field generated from outside a body when the implantable pump is implanted in the body.

2. The implantable pump of claim 1, wherein a layer of the plurality of layers is a membrane configured to function as an inlet check valve and/or an outlet check valve.

3. The implantable pump of claim 1, wherein a stroke of the magnetic element is mechanically limited to assure consistent pump stroke volume under a range of magnetic field strength.

4. The implantable pump of claim 1, further comprising an implantable catheter in fluid communication with an outlet port of the implantable pump and configured to deliver the fluid from the outlet port to a specific anatomical site.

5. The implantable pump of claim 1, further comprising a controller separate from the implantable pump and configured to generate the magnetic field to cause the implantable pump to function, wherein the controller comprises a magnetic field generating system, a power supply, and a user interface configured for programming and monitoring fluid delivery, and an indication of proper positioning of the implantable pump.

6. A fluid delivery system for localized delivery of medical agents and drugs comprising:
   an implantable pump, the pump comprising:
      a plurality of layers bonded to each other so as to form a laminate assembly, the laminate assembly having a cavity defined therein for passage of a fluid therethrough;
      an inlet port in communication with the cavity; and
      an outlet port in fluid communication with the cavity;
      at least one check valve disposed within the laminate assembly; and
      a magnetic element configured to cause the pump and/or the at least one check valve to function in response to a magnetic field, the magnetic element being separated by a flexible diaphragm into a first magnet portion and a second magnet portion; and
   a controller being separate from the pump and being configured to generate a magnetic field to cause the pump to function.

7. The fluid delivery system of claim 6, wherein a stroke of the magnetic element is mechanically limited to assure consistent pump stroke volume under a range of magnetic field strength.

8. The fluid delivery system of claim 6, further comprising an implantable catheter in fluid communication with the outlet port and configured to deliver the fluid from the outlet port to a specific anatomical site.

9. The fluid delivery system of claim 6, wherein the controller comprises a magnetic field generating system, a power supply, and a user interface configured for programming and monitoring fluid delivery, and an indication of proper positioning of the pump.

10. A fluid delivery system for localized delivery of medical agents and drugs comprising:
   an implantable pump comprising a plurality of layers bonded to each other so as to form a laminate assembly, the laminate assembly having a cavity defined therein for passage of a fluid therethrough, a magnetic element configured to cause the implantable pump to function in response to a magnetic field, the magnetic element being separated by a flexible diaphragm into a first magnet portion and a second magnet portion, an inlet port in communication with the cavity, and an outlet port in fluid communication with the cavity;
   a fluid reservoir in fluid communication with the inlet port; and
   a controller, separate from the implantable pump and the reservoir, and configured to generate a magnetic field to cause the pump to function.

11. The fluid delivery system of claim 10, further comprising an implantable catheter in fluid communication with the outlet port and configured to deliver the fluid from the outlet port to a specific anatomical site.

12. The fluid delivery system of claim 10, wherein both the implantable pump and the reservoir contain no biologically hazardous materials.

13. The fluid delivery system of claim 10, further comprising an implantable catheter in fluid communication with the inlet port and the reservoir.

14. The fluid delivery system of claim 10, further comprising an enclosure housing the implantable pump and/or the reservoir.

15. The fluid delivery system of claim 14, wherein the enclosure comprises one or more septums configured to provide access to the reservoir through percutaneous injection so as to enable aspirating fluid from the reservoir and filling the reservoir with fluid.

16. The fluid delivery system of claim 10, wherein the controller comprises a magnetic field generating system, a power supply, and a user interface configured for programming and monitoring fluid delivery, and an indication of proper positioning of the implantable pump.

17. The fluid delivery system of claim 16, wherein the magnetic field generating system of the controller is configured to generate a reversing magnetic field, an oscillating magnetic field, or a combination thereof.

18. The fluid delivery system of claim 16, wherein the user interface is configured to monitor magnetic flux and to indicate whether the magnetic element is moving.

19. The fluid delivery system of claim 10, wherein a layer of the plurality of layers is a membrane configured to function as an inlet check valve and/or an outlet check valve to control flow through the cavity, the inlet port and the outlet port.

20. The fluid delivery system of claim 10, wherein a stroke of the magnetic element is mechanically limited to assure consistent pump stroke volume under a range of magnetic field strength.

* * * * *